United States Patent [19]

Smith et al.

[11] Patent Number: 5,913,875

[45] Date of Patent: *Jun. 22, 1999

[54] TAPER POINT NEEDLE

[75] Inventors: Daniel J. Smith, Manalapan Township; Surjit S. Gill, Bridgewater, both of N.J.; Eric Hinrichs, Pipersville, Pa.; Thomas Nering, Milford, N.J.

[73] Assignee: Ethicon, Inc., Somerville, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/655,372

[22] Filed: May 30, 1996

[51] Int. Cl.$^6$ .................................................. A61B 17/06

[52] U.S. Cl. ...................... 606/222; 606/223; 112/80.03; 289/16

[58] Field of Search ..................................... 606/222, 223, 606/224–227; 112/80.03, 222; 289/16

[56] References Cited

U.S. PATENT DOCUMENTS

| | | | |
|---|---|---|---|
| 5,100,432 | 3/1992 | Matsutani | 606/223 |
| 5,330,441 | 7/1994 | Prasad et al. | 606/222 |
| 5,342,397 | 8/1994 | Guido | 606/222 |

*Primary Examiner*—Michael Buiz
*Assistant Examiner*—Tina T. D. Pham
*Attorney, Agent, or Firm*—Emil Richard Skula

[57] ABSTRACT

A taper point surgical suture needle. The suture needle is an elongated member having a proximal suture mounting end and a distal piercing point. The elongated member has a first tapered region adjacent to the piercing point having a taper ratio of about 12:1. The member also has a second tapered region adjacent to the first tapered region having a taper ration of from about 6:1 to about 11:1. And, the member additionally has a third region adjacent to the second tapered region having a taper ratio of at least about 12:1.

18 Claims, 6 Drawing Sheets

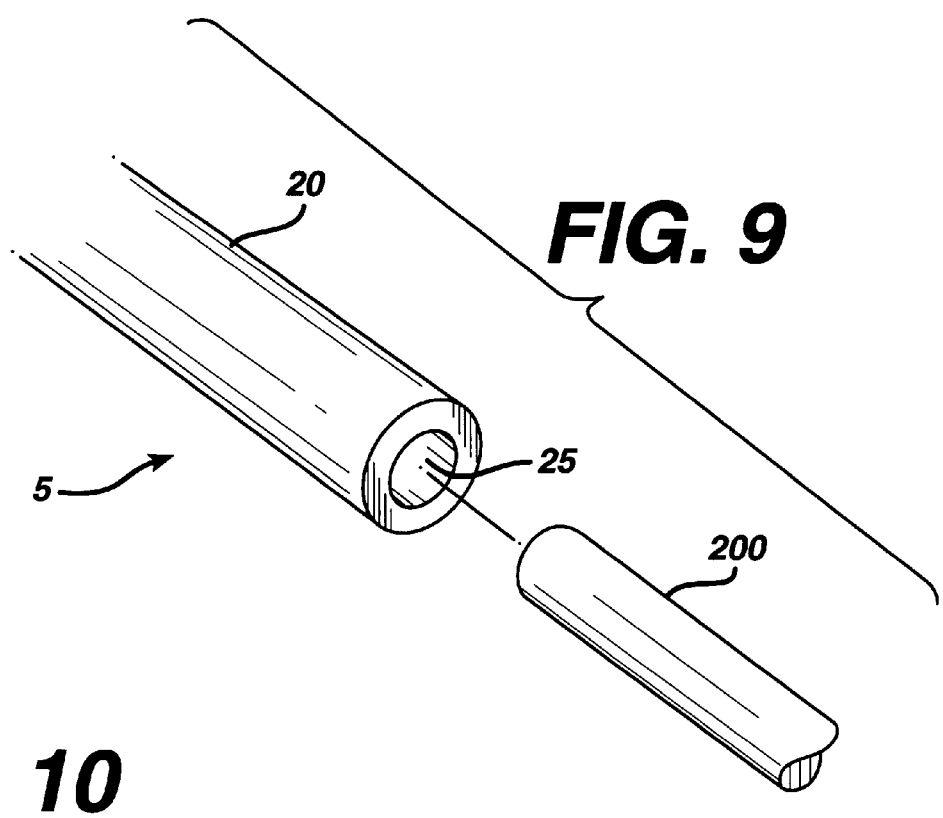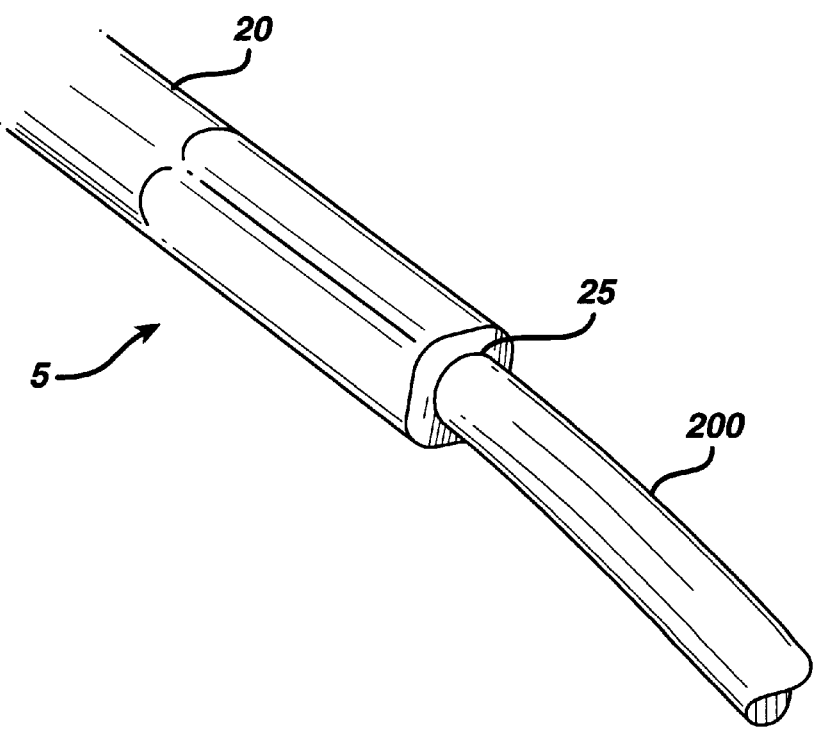

TAPER POINT NEEDLE

FIELD OF THE INVENTION

The field of art to which this invention relates is surgical needles, in particular, taper point surgical needles.

BACKGROUND OF THE INVENTION

Surgical needles are well known in the medical arts. The needles typically have a curved, elongated body with a distal piercing point and a proximal suture mounting end. Sutures may be mounted either into holes drilled into the proximal ends of the needle or channels stamped into the proximal ends of the needles. Sutures are mounted to the drilled holes or channels through a conventional swaging process wherein the proximal end of a needle is stamped or hit with a die thereby compressing the suture within the hole or channel.

Although there are a variety of surgical needles known in this art, two types of conventional surgical needles are widely and typically used. These needles include taper point needles and cutting edge needles. Taper point needles taper to a distal piercing point and have a smooth outer surface. Cutting edge needles also taper to a piercing point and have one or more cutting edges with an otherwise smooth outer surface. As mentioned previously, taper point needles and cutting edge needles and methods of manufacturing these needles are known in the art and are disclosed for example in commonly owned U.S. Pat. No. 5,477,604 and commonly owned copending U.S. patent application Ser. No. 08/633,607, which are incorporated in their entirety by reference. Taper point surgical needles typically have a taper from a middle section of the needle body which ends in a distal piercing point. The taper is often expressed as a ratio of the length of the taper section to the diameter of the wire used to form the needle, e.g., 12D/1D or 12:1. It is known that the higher the taper ratio is, the more slender the taper, and the resistance to penetration through tissue will typically be lessened. However, the more slender the taper, the less will be the mechanical strength for needles manufactured from the same material. The converse is also to be expected for needles having lower taper ratios. Taper point needles having taper ratios of 8:1 or smaller were, in the past, the industry standard. Today, most taper point needles have a 12:1 taper ratio.

There is a constant need in this art for improved surgical needles having good penetration characteristics (i.e., resistance to penetration through tissue) and good mechanical characteristics such as bending strength, etc. There is also a constant need in this art for taper point needles which have configurations that are readily manufactured in an automated manufacturing process.

SUMMARY OF THE INVENTION

Accordingly, it is an object of the present invention to provide taper point surgical needles having good resistance to penetration in tissue along with good mechanical properties.

It is a further object of the present invention to provide a taper point surgical needle having a substantially parabolic or straight profile which is easy to manufacture in automated needle manufacturing processes including, for example, stamping/coining processes and/or grinding.

Therefore, a taper point surgical needle is disclosed. The surgical needle consists of an elongated member, having a proximal end and a distal end. A piercing point extends from the distal end of the member. A suture mounting means extends from the proximal end of the member. The elongated member has a first tapered segment adjacent to the piercing point, said segment having a substantially parabolic or straight profile and further having a taper ratio of at least 12:1. The member also has a second tapered segment adjacent to the first tapered segment, said segment having a substantially parabolic or straight profile and further having a taper ratio of from about 6:1 to about 11:1. And, the member additionally has a third tapered segment adjacent to the second tapered segment, said third segment having a substantially parabolic or straight profile and further having a taper ratio of about at least 12:1.

Yet another aspect of the present invention is a cutting edge surgical needle having cutting edges. The surgical needle consists of an elongated member, having a proximal end and a distal end. A piercing point extends from the distal end of the member. A suture mounting means extends from the proximal end of the member. The elongated member has a first tapered segment adjacent to the piercing point, said segment having a substantially parabolic or straight profile and further having a taper ratio of at least 12:1. The member also has a second tapered segment adjacent to the first tapered segment, said segment having a substantially parabolic or straight profile and further having a taper ratio of from about 6:1 to about 11:1. And, the member additionally has a third tapered segment adjacent to the second tapered segment, said third segment having a substantially parabolic or straight profile and further having a taper ratio of about at least 12:1.

Still yet another aspect of the present invention is a method of approximating mammalian tissue using the above-described surgical needles and surgical sutures Other features and advantages of the surgical needles of the present invention will become more apparent from the following description and accompanying drawings.

BRIEF DESCRIPTION OF THE DRAWINGS

FIG. 8 is an enlarged top plan view of a needle of the present invention having a blunt tip.

FIGS. 9 and 10 are perspective views showing the proximal needle mounting ends of needles of the present invention having proximal drilled suture mounting ends.

DETAILED DESCRIPTION OF THE INVENTION

Figure 1:
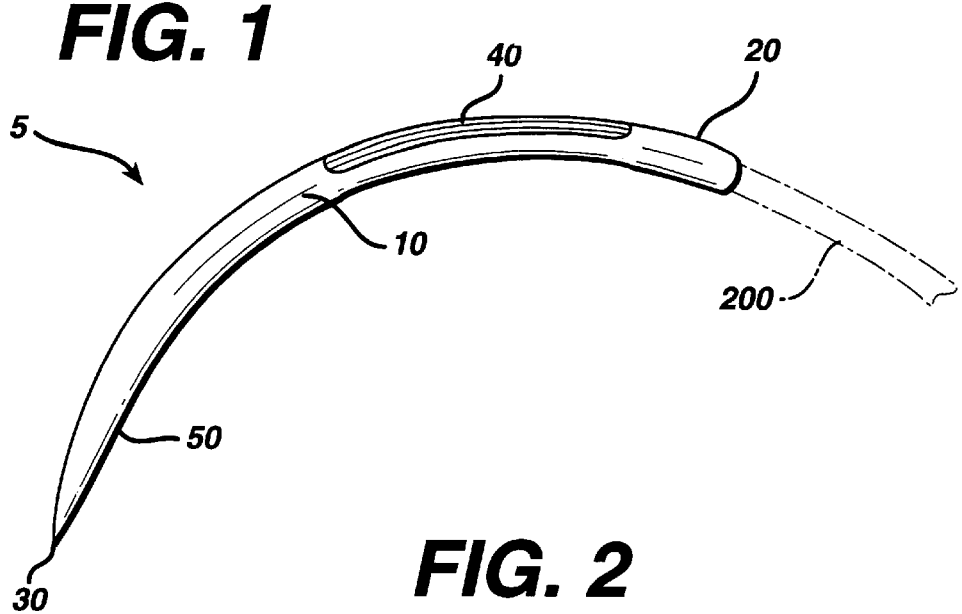
FIG. 1 is a perspective view of a surgical needle of the present invention having a drilled proximal suture mounting cavity.
Figure 2:
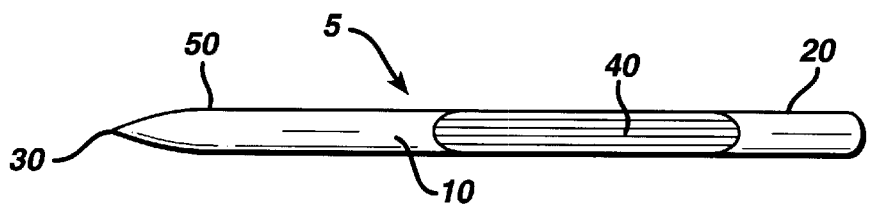
FIG. 2 is a top view of the surgical needle of FIG. 1.
Figure 3:
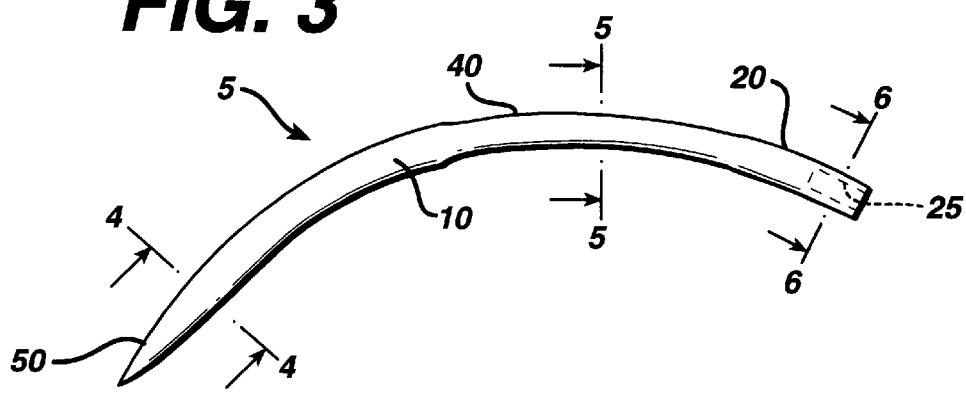
FIG. 3 is a side view of the surgical needle of FIG. 2.
Figure 4:
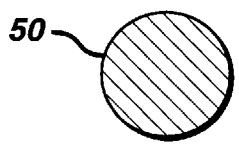
FIG. 4 is a cross-sectional view of the needle of FIG. 3 taken along View Line 4—4.
Figure 5:
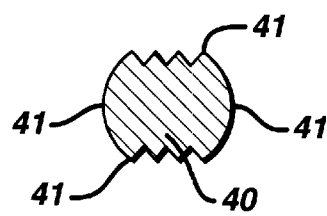
FIG. 5 is a cross-sectional view of the surgical needle of FIG. 3 taken along View Line 5—5.
Figure 6:
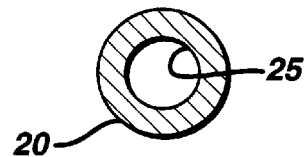
FIG. 6 is a cross-sectional view of the surgical needle of FIG. 3 taken along View Line 6—6.
Figure 11:
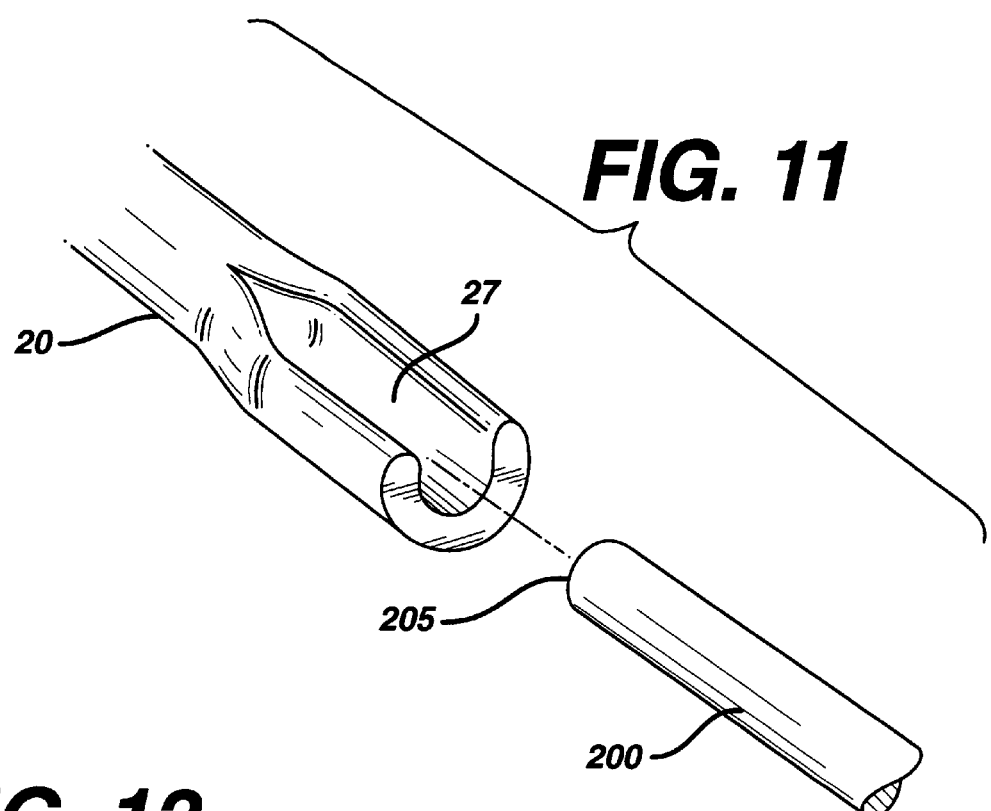
FIGS. 11 and 12 are perspective views showing the proximal needle mounting ends of needles of the present invention having proximal channel suture mounting ends.
Figure 12:
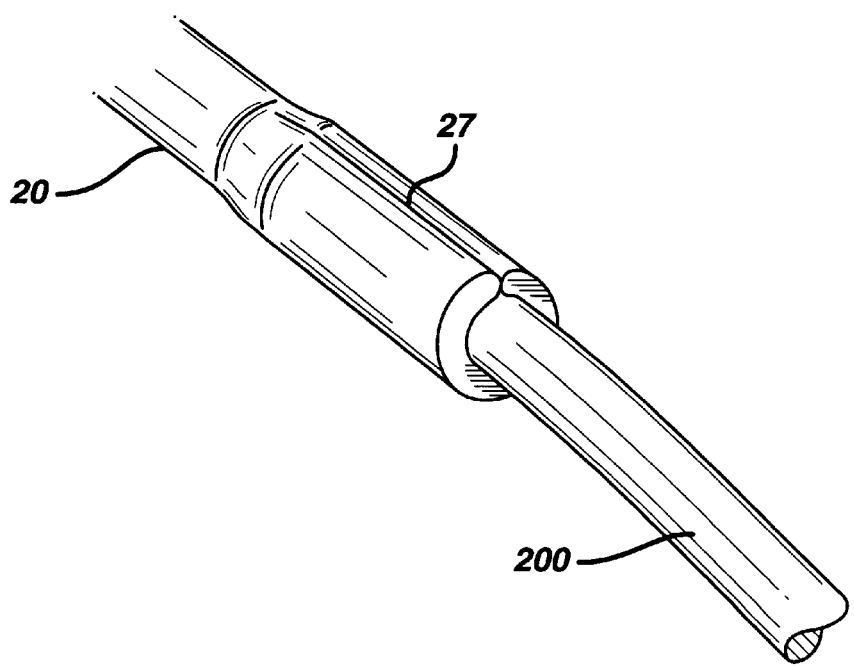

As can be seen in FIGS. 1–10, the taper point needle 5 of the present invention is seen to be an elongated member 10, having a proximal section 20, a distal section 50, and a central section 40. The needle 5 is seen to have distal piercing tip 30. Although FIG. 1 shows a conventional curvature of the elongated member 10, it will be appreciated by those skilled in the art that the elongated member 10 may have other conventional curvatures including compound, straight, or ¼, ⅜, ½ or ⅝ type curvatures or the elongated member may be straight or have straight and curved sections. As seen in FIG. 5 central section 40 has a generally flattened cross-section having opposed ribbed surfaces 41. If desired, the cross-section of central section 40 may have other conventional configurations including square, rectangular (in the x and y direction), circular, oval, triangular, I-beam, ribbon and the like. The cross-section of central section 40 will preferably be such that a conventional needle-grasper can sufficiently grasp and effectively maintain the needle 5 in a fixed position as the needle 5 penetrates body tissue, thereby preventing the needle from slipping between the jaws of the needle grasper. Referring to FIG. 6, proximal end section 20 is seen to have a circular configuration, having a central drilled suture mounting hole 25. A conventional surgical suture 200 is illustrated in phantom in FIG. 1 mounted in suture mounting hole 25 of needle 5. A suture 200 is mounted in hole 25 using conventional drilled swaging processes, as seen in FIGS. 9 and 10. And, as seen in FIGS. 11 and 12, the proximal end 20 of the needle 5 may also have a conventional channel section 27 for receiving and mounting a suture 200. The drilled hole 25 or the channel 27 is illustrated in FIGS. 10 and 12, respectively, after the distal tip 205 of the suture 200 has been mounted and swaged in a conventional manner therein. The suture mounting hole 25 is drilled in a conventional manner using conventional drilling equipment including mechanical tool steels or carbide oil coated drills, lasers, and the like and combinations thereof. Channel 27 is formed using a conventional forming process wherein the channel is formed using conventional dies and punches. The needles 5 of the present invention may have conventional sharp or blunt piercing points. Blunt tip needles may be used in the operating room as part of a safety program to reduce the incidence of the transmission of infectious disease.

Figure 7:
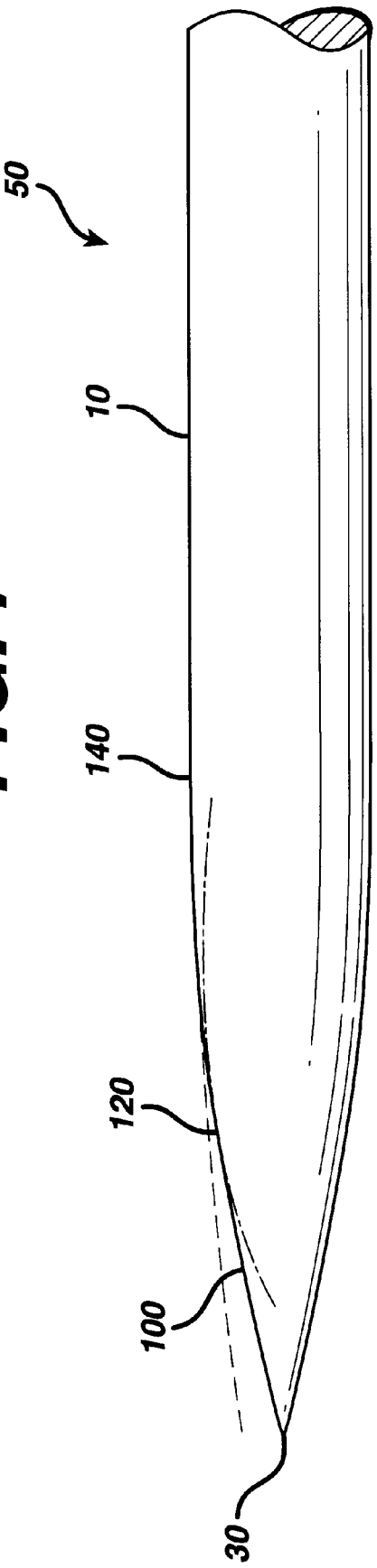
FIG. 7 is an enlarged top plan view of the distal end of the needle of FIGS. 1 and 2.

Referring now to FIGS. 1, 7 and 8, the elongated member 10 is seen to have, in distal section 50, first tapered segment 100 adjacent to piercing tip 30. The segment 100 has a substantialy parabolic profile. The section 100 has a taper ratio of at least 12:1, preferably 12:1. Those skilled in the art will appreciate that the length of the tapered segment 100, as well as tapered segments 120 and 140, will vary in accordance with the size of the needle wire used, the strength and penetration characteristics desired (i.e., tissue piercing, resistance to bending, ease of penetration and the like, etc.). For example, for a needle having a needle wire with a diameter of 0.040", the length of segment 100 will be about 0.005" to about 0.035", more typically about 0.010" to about 0.030, and preferably about 0.015" to about 0.025". The elongated member, 10 is also seen to have second tapered segment 120 adjacent to first tapered segment 100, wherein segment 120 also has a substantially parabolic profile. The section 120 has a taper ratio of from about 6:1 to about 11:1, more typically about 7:1 to about 10:1, and preferably about 8:1. The length of the tapered segment 120 will, for a needle having a wire size of 0.040", be about 0.100" to about 0.340", more typically about 0.140" to about 0.300", and preferably about 0.180" to about 0.260". The elongated member, 10 is also seen to have third tapered segment 140 adjacent to second tapered segment 120. The section 140 also has a substantially parabolic profile and further has a taper ratio of at least 12:1, preferably about 12:1. The length of the tapered region 140 will, as previously stated depend upon several factors, and for a needle having a wire diameter of 0.040" will typically be, for example, about 0.120" to about 0.360", more typically about 0.160" to about 0.320", and preferably about 0.200" to about 0.280". The lengths of the segments 100, 120 and 140 for needles of the present invention having different diameter sizes will preferably be proportional to those listed above, although they may differ. It will be appreciated by those skilled in the art that there will be transition sections between adjoining tapered segments wherein the taper ratios will be transitioning, either higher or lower. It is preferred to make the lengths of the transition sections sufficiently long to effectively provide for a smooth transition between segments without adversely affecting mechanical strength and resistance to penetration The term parabolic profile is defined to mean a profile of a needle which curves in a conventional substantially parabolic manner or the like. It will be appreciated by those skilled in the art that the profile of the needles of the present invention may have, although not preferred, a conventional, substantially straight profile.

As seen in FIG. 8, the needles of the present invention may have blunt distal piercing points. A needle 250 of the present invention is seen to have elongated member 252 having blunt piercing tip 255, and first, second and third tapered segments 260, 265 and 270 respectively.

As mentioned previously, the needles of the present invention will have three adjacent tapered segments. The first tapered segment will be located immediately adjacent to the distal piercing tip of the needle, and will have a taper ratio of at least 12:1. The second tapered segment will be adjacent to, and proximal to, the first segment and will have a taper ratio of about 6:1 to about 11:1, The third segment will be proximal to and adjacent to the second segment and will have a taper ratio of at least 12:1.

Figure 13:
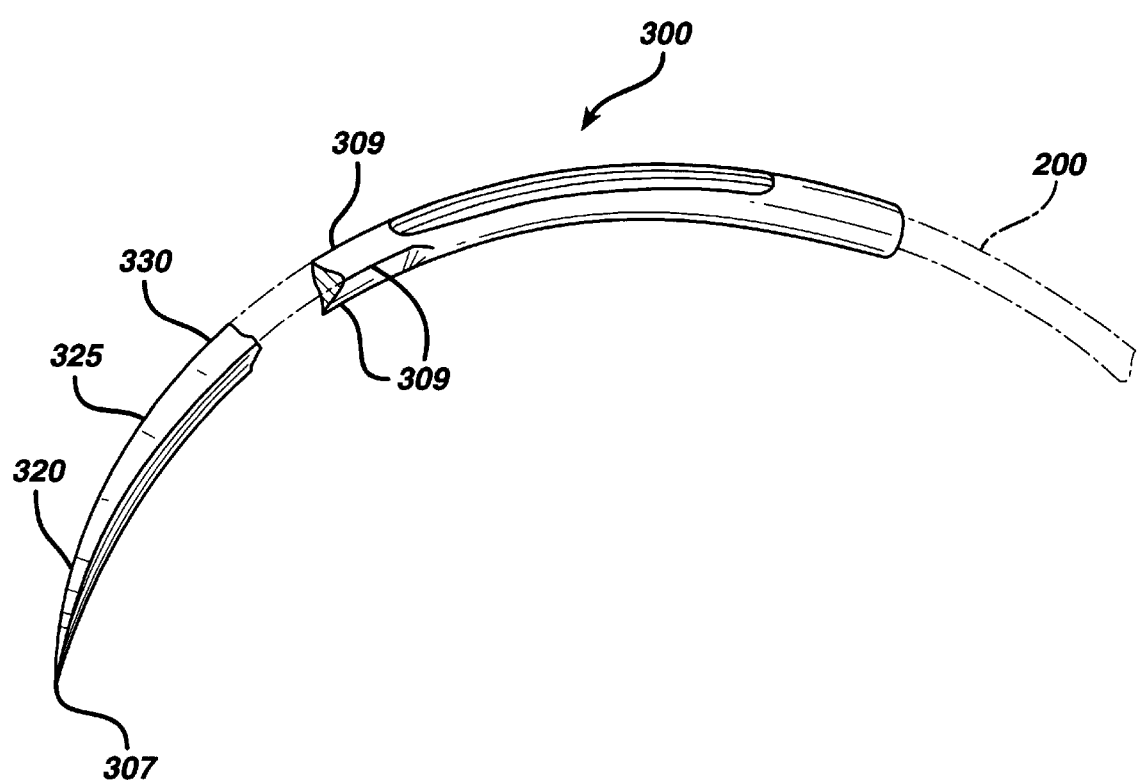
FIG. 13 is a perspective view of a needle of the present invention having cutting edges.

FIG. 13 illustrates a needle 300 of the present invention having elongated member 305 having piercing tip 307 and cutting edges 309. The member 305 is seen to have first, second and third tapered segments 320, 325 and 330, respectively.

The needles 5 of the present invention will be manufactured in a variety of sizes, curved configurations and wire diameters. The exact size and curvature of the needles of the present invention is, of course, a matter of choice. The diameter of the needle wire used to manufacture the needles of the present invention will depend upon the particular needle size and intended use. For example, the needle wire may have a diameter ranging from 0.001 inches to about 0.100 inches, more typically about 0.010 inches to about 0.080 inches, preferably about 0.015 inches too about 0.040 inches. However, other smaller and larger wire diameters may be used. The length of the needles of the present invention will vary in accordance with several parameters including the wire alloy, the wire diameter the desired finished length and the type of needle. When the needles 5 of the present invention are preferably curved, then the radius of curvature will generally be, for example anywhere from 0.050 inches to about 6 inches. The length of the arc will be anywhere, depending on choice, from about ¼ to about ⅝ of a circle, as mentioned hereinabove. By choice, some needles will remain straight. Optionally the needles of the present invention can have combinations of curved and straight sections. The needles of the present invention may be made from conventional alloys including 300 series stainless steel, 400 series stainless steel or any other alloys or materials (e.g., polymers, ceramics, etc.) which can be formed into a needle or equivalents thereof having sufficient mechanical characteristics to produce a needle which effectively functions. The needles may also be made from alloys such as those disclosed in commonly owned U.S. Pat. No. 5,000,912 which is incorporated by reference.

The needles of the present invention may be made using taper point surgical needle apparatuses and manufacturing methods including die forming, die casting, powdered metal molding, grinding, and machining. It is preferred to manufacture the needles of the present invention using equipment and processes as disclosed in commonly-owned, co-pending U.S. patent application No. 08/633,607 and commonly owned U.S. Pat. No. 5,477,604 which are incorporated herein by reference.

The following example is illustrative of the principles and practice of the present invention.

EXAMPLE

Taper point surgical needles 10 of the present invention were manufactured using conventional needle manufacturing techniques. The needles had a distal region with a first tapered segment adjacent to the piercing point having a 12:1 taper ratio, a second adjacent tapered segment having an 8:1 taper ratio, and a third adjacent segment having a 12:1 taper ratio. Other needles were similarly manufactured having distal ends with conventional 12:1 taper ratios and distal ends with conventional 8:1 taper ratios. The needles were subjected to conventional bend testing and penetration testing. The needles were bend tested at 0.1025" from the piercing point to determine bending force through 90 degrees. The results of the testing are indicated in the table.

TABLE

| Needle Type | 1st Pass Penetration/ Std Dev. | Avg of All Over all 10- Pass Penetration Dev. | Average Cross-Section | Average Peak Value | Total Bend | Average Size |
|---|---|---|---|---|---|---|
| Conventional 8:1 | 210/31 gms | 414/74 gms | .03109" | 1964.5 gms | 90° | .039 |
| Conventional 12:1 | 168 gms | 212 gms | .02479" | 1086.1 gms | 90° | .039 |
| Needle of Present Invention 12:1/8: 1/12:1 | 183 gms | 217 gms | .029515" | 1835.4 gms | 90° | .039 |

The results of the testing showed that, surprisingly and unexpectedly, the needles of the present invention had almost identical resistance to penetration to standard 12:1 taper ratio needles, with almost the strength of a conventional 8:1 taper ratio needle.

The surgical needles of the present invention are believed to have the several surprising and unexpected advantages including ease of tissue penetration and improved tip strength, reduced tissue trauma, and better cosmetic results.

The needles of the present invention when mounted to conventional surgical sutures are used in a conventional manner in conventional surgical procedures to pass through and approximate mammalian tissue. In such procedures, the needle is typically held in a conventional needle grasper. The needles of the present invention have superior tip strength similar to that associated with, for example, an 8:1 taper point with resistance to penetration which is similar to the resistance to penetration of, for example, a 12:1 taper point needle. It is surprising and unexpected that the needles of the present invention approach the penetration resistance of slender needles while retaining nearly the strength of heavier needles.

Although this invention has been shown and described with respect to detailed embodiments thereof, it will be understood by those skilled in the art that various changes in form and detail thereof may be made without departing from the spirit and scope of the claimed invention.

We claim:

1. A surgical needle having a taper point, comprising:
   an elongated member having a proximal end and a distal end and a distal piercing point, wherein said distal end comprises:
   I. a first tapered segment adjacent to the piercing point having a taper ratio of at least about 12:1;
   II. a second tapered segment adjacent to the first tapered region having a taper ratio of from about 6:1 to about 11:1; and,
   III. a third tapered segment adjacent to the second tapered segment having a taper ratio of from about at least about 12:1; and,
   a suture-mounting means in the proximal end of the member.

2. The needle of claim 1 wherein the elongated member is curved.

3. The needle of claim 1 wherein the length of the first segment is about 0.005" to about 0.035".

4. The needle of claim 1 wherein the length of the second tapered segment is about 0.100" to about 0.340".

5. The needle of claim 1 wherein the length of the third tapered region is about 0.120" to about 0.360".

6. The needle of claim 1 wherein the suture-mounting means comprises a drilled cavity.

7. The needle of claim 1 wherein the suture-mounting means comprises a channel.

8. The needle of claim 1 wherein the piercing point comprises a blunt tip.

9. The needle of claim 1 wherein the piercing point comprises as sharp piercing point.

10. The needle of claim 1 wherein the elongated member comprises at least one curved section and at least on straight section.

11. The needle of claim 1 wherein the elongated member is straight.

12. The needle of claim 1, additionally comprises cutting edges.

13. The needle of claim 1 wherein the first tapered segment has a taper ratio of 12:1.

14. The needle of claim 1 wherein the second tapered segment has a taper ratio of about 6:1 to about 11:1.

15. The needle of claim 1 wherein the third tapered segment has a taper ratio of 12:1.

16. The needle of claim 1 wherein each segment comprises a substantially parabolic profile.

17. The needle of claim 1 wherein each segment comprises a substantially straight profile.

18. A method of approximating mammalian tissue, said method comprising:

inserting a surgical needle having an attached surgical suture through mammalian tissue thereby approximating the tissue, wherein the surgical needle comprises:

an elongated member having a proximal end and a distal end and a distal piercing point, wherein the distal end comprises:

I. a first tapered segment adjacent to the piercing point having a taper ratio of at least about 12:1;

II. a second tapered segment adjacent to the first tapered region having a taper ratio of from about 6:1 to about 11:1; and, III. a third segment adjacent to the second tapered region having a taper ratio of about 12:1; and, a suture-mounting means in the proximal end of the member.

* * * * *